United States Patent
Tarng et al.

(10) Patent No.: US 10,835,622 B2
(45) Date of Patent: Nov. 17, 2020

(54) MODE OF INDUCING RENAL TRANSPLANT REJECTION ON ANIMALS AND ITS MANUFACTURING APPROACH

(71) Applicants: National Yang-Ming University, Taipei (TW); Taipei Veterans General Hospital, Taipei (TW); Taichung Veterans General Hospital, Taichung (TW)

(72) Inventors: Der-Cheng Tarng, Taipei (TW); Nien-Jung Chen, Taipei (TW); Shuo-chun Weng, Taichung (TW)

(73) Assignees: NATIONAL YANG-MING UNIVERSITY, Taipei (TW); TAIPEI VETERANS GENERAL HOSPITAL, Taipei (TW); TAICHUNG VETERANS GENERAL HOSPITAL, Taichung (TW)

( * ) Notice: Subject to any disclaimer, the term of this patent is extended or adjusted under 35 U.S.C. 154(b) by 494 days.

(21) Appl. No.: 15/671,919

(22) Filed: Aug. 8, 2017

(65) Prior Publication Data
US 2018/0326096 A1 Nov. 15, 2018

(30) Foreign Application Priority Data
May 12, 2017 (TW) .............................. 106115825 A

(51) Int. Cl.
*A61K 49/00* (2006.01)
*C12N 5/0783* (2010.01)
*A01K 67/027* (2006.01)

(52) U.S. Cl.
CPC ...... *A61K 49/0008* (2013.01); *A01K 67/0271* (2013.01); *C12N 5/0636* (2013.01); *C12N 5/0637* (2013.01); *C12N 5/0638* (2013.01); *A01K 2207/12* (2013.01); *A01K 2227/105* (2013.01); *A01K 2267/0325* (2013.01); *C12N 2502/1114* (2013.01); *C12N 2502/1121* (2013.01)

(58) Field of Classification Search
None
See application file for complete search history.

(56) References Cited

U.S. PATENT DOCUMENTS

2016/0003856 A1 1/2016 Lovat et al.

*Primary Examiner* — James D Schultz
(74) *Attorney, Agent, or Firm* — Muncy, Geissler, Olds & Lowe, P.C.

(57) ABSTRACT

The invention is a simplified model on kidney rejection in animals and its setting approach. The method involves isolating dendritic cells from male mice and isolating T cells from female mice and then using the naive T cells in vitro to culture concurrently with male dendritic cells. Those activated T cells from female origin were injected into renal cortex in male mice for the purpose of attacking renal cortex. The animal model simulates the renal transplant rejection method to enable effective induction of renal transplant immune reaction.

10 Claims, 7 Drawing Sheets

MODE OF INDUCING RENAL TRANSPLANT REJECTION ON ANIMALS AND ITS MANUFACTURING APPROACH

CROSS-REFERENCE TO RELATED APPLICATIONS

This application claims priority to Taiwan Application Serial No. 106115825, filed in May 12, 2017, the content of which is hereby incorporated by reference in its entirety.

FIELD OF THE INVENTION

The present invention is related to a simplified model on kidney rejection in animals and a method of creating the animal model, which comprises: isolating dendritic cells from male mice; isolating T cells from female mice; activating these dendritic cells in vitro; administrating these activated T cells (the activated T cells have a function of Y chromosome memory on the rodent cells in order to attack) into the renal cortex, to let the activated T cells attack the renal cortex of the male mice, in order to induce the renal transplant rejection effectively.

BACKGROUND OF THE INVENTION

Kidney transplantation is the best treatment for renal failure, but the risk of kidney transplantation is very high. When a solid organ was transplanted into a body, the body's human immune system would take the foreign kidney as an invader and thus attack the transplanted kidney just like rejection. Therefore, the foreign kidney would lose its function and then result in necrosis. As far as the surgery and therapy are concerned, kidney transplantation is not too complicated; however, how to control recipient's own immune system is the bottleneck process. Thus, the anti-rejection drugs are needed for suppressing the natural immune system function during the kidney transplantation. Nevertheless, the patients still have acute and chronic renal transplant rejection after administration of traditional immunosuppressive agents. The most important part before developing an immunosuppressive agent is to develop a simple and stable renal transplant rejection animal model for testing new drugs.

The traditional method of renal transplant rejection in animal model is to implant organs between different mouse species which needs vascular anastomosis. However, this method is likely to cause intraoperative or postoperative bleeding after vascular anastomosis. The survival rate was low because the transplanted organ would be easily wrapped by mesentery and lose its function.

In addition, the renal transplantation in the previous literature is co-culturing the renal tubular epithelial cell lines with allogeneic lymphocytes in a cell model, but this model has high variability and cannot be applied to organisms.

Therefore, it is important to establish a rejection model that could be applied to the organism and does not require the complicated vascular anastomosis. It is necessary to combine the renal transplant rejection model and the cell model to establish a highly stable model to replace the existing vascular anastomosis.

The present invention is related to a simple animal transplant rejection model after injecting activated female T cells into the renal cortex of the male mouse. Although the isolated T cells can be used for specific immunization has been revealed by US 20160003856, but the T cell line of US 20160003856 is administered to an in vitro skin model rather than in a living animal (such as mouse). Besides, the usage of skin allergy testing is different from the animal model of organ transplant rejection.

Therefore, it is necessary and urgent to improve the traditional kidney transplant procedure which is time-consuming with high animal mortality and lack of reproducibility and stability. In addition, developing new immunosuppressive agents or immunomodulators can prevent renal transplant rejection through effectively revealing the underlying mechanism.

SUMMARY OF THE INVENTION

The present invention is related to a simple animal organ transplant rejection model comprising a method: isolating dendritic cells from male mice; isolating T cells from female mice; activating these T cells by dendritic cells in vitro; administrating these activated T cells (the activated T cells have a function of Y chromosome memory on the rodent cells in order to attack target organs) into the renal cortex, to let the activated female T cells attack the renal cortex of the male mice. The above method is used in order to induce rejection in renal transplantation effectively.

The present invention provide a method for preparing an animal model simulating the transplant immune rejection reaction, which includes: (a) Providing a dendritic cell, wherein the dendritic cell is obtained from a first animal subject; (b) Providing a lymphocyte, wherein the lymphocyte is selected from a second animal subject; (c) Co-culturing the dendritic cell and the lymphocyte in vitro to form an activated T lymphocyte; (d) Creating an implant position in renal cortex of an third animal subject; and (e) Transplanting the activated T lymphocyte into the implant position in renal cortex of an third animal subject. Wherein the first subject, the second subject, and the third subject are the same species, and the activated T lymphocyte would attack the renal cortex after transplanting the implant position in renal cortex of the third animal subject. Thus the animal model of transplant rejection would be induced in the third animal subject.

In one embodiment of the present invention, wherein the first animal subject, the second animal subject, and the third animal subject are mice.

In one embodiment of the present invention, wherein the gender of the first animal subject and the second animal subject are different.

In one embodiment of the present invention, wherein the first animal subject is a male mouse and the second animal subject is a female mouse.

In one embodiment of the present invention, wherein the implant position is a tunnel or a pouch.

In one embodiment of the present invention, wherein the T lymphocyte belongs to a $CD4^+$ or $CD8^+$ entity.

In one embodiment of the present invention, wherein the dendritic cell is obtained from the thigh bone marrow of the first animal subject.

In one embodiment of the present invention, wherein the dendritic cell is obtained from the lymph node of the second animal subject.

In one embodiment of the present invention, wherein the depth of the tunnel or the pouch is 0.5 cm.

In one embodiment of the present invention, wherein the age of the mouse is 6-10 weeks old.

The present invention provides an animal model of inducing the transplant rejection and immune reaction which activated T lymphocytes are injected into the renal cortex of the third animal subject.

DETAILED DESCRIPTION OF THE INVENTION

Figure 1:
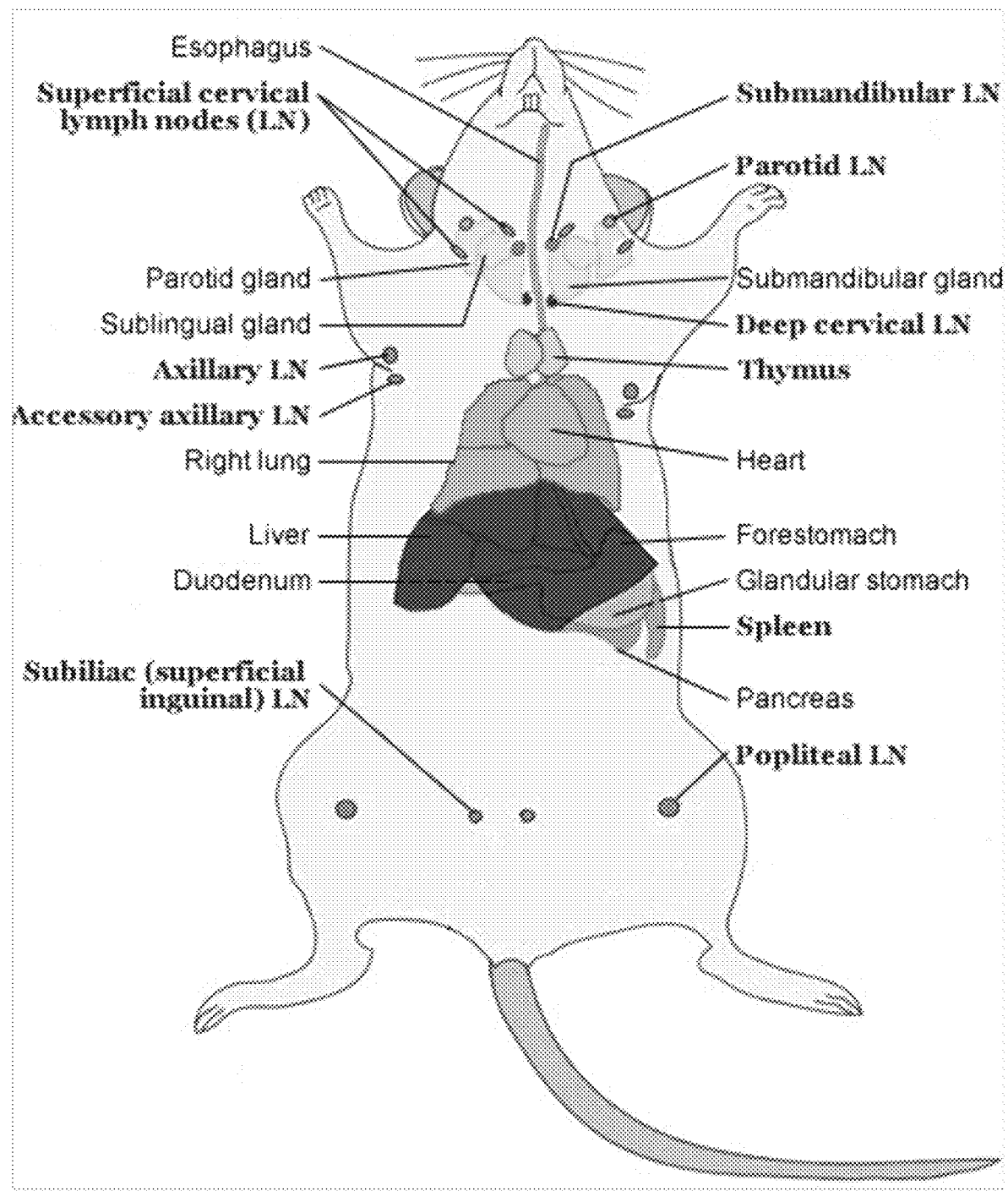
FIG. 1 shows the picture of dendritic cells from the bone marrow of male mouse and T lymphocytes of female mouse.
Figure 2:
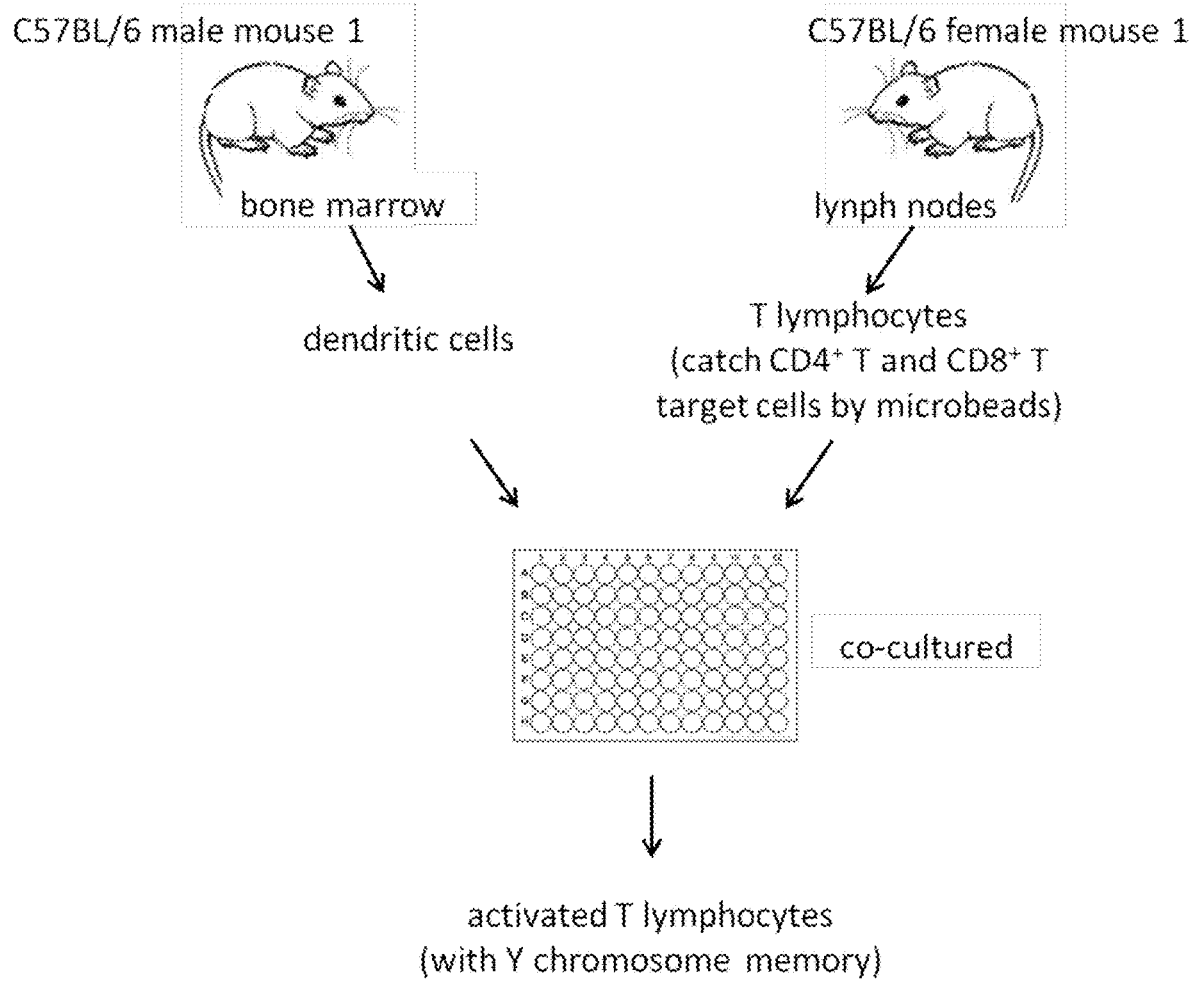
FIG. 2 shows the flow chart of in vitro culture and production of activated T lymphocytes.

Example 1: Creating and Culturing an Activated T Lymphocyte Platform In Vitro Culturing Activated T-Lymphocytes In Vitro The dendritic cells of the male mouse C57BL/6 were rushed out of the bone marrow (as shown in FIG. 1), and the dendritic cells were cultured in 6 ml Roswell Park Memorial Institute (RPMI) medium and granulocyte-macrophage colony-stimulating factor (GM-CSF) (20 ng/mL) for 9 days, and dendritic cells were stimulated with 100 ng/ml lipopolysaccharide (LPS) on the 9th day for about 24 hours; The lymph nodes of the mouse C57BL/6 were found out, and the T lymphocytes were obtained (as shown in FIG. 1). $CD4^+$ and $CD8^+$ T cells were selected from these T lymphocytes by microbeads. Then, the dendritic cells and selected $CD4^+$ and $CD8^+$ T cells were co-cultured for 13 days to obtained the activated T lymphocytes (with Y chromosome memory) in vitro (FIG. 2).

Example 2: Transplantation of Cultured T Lymphocytes In Vitro

Figure 3:
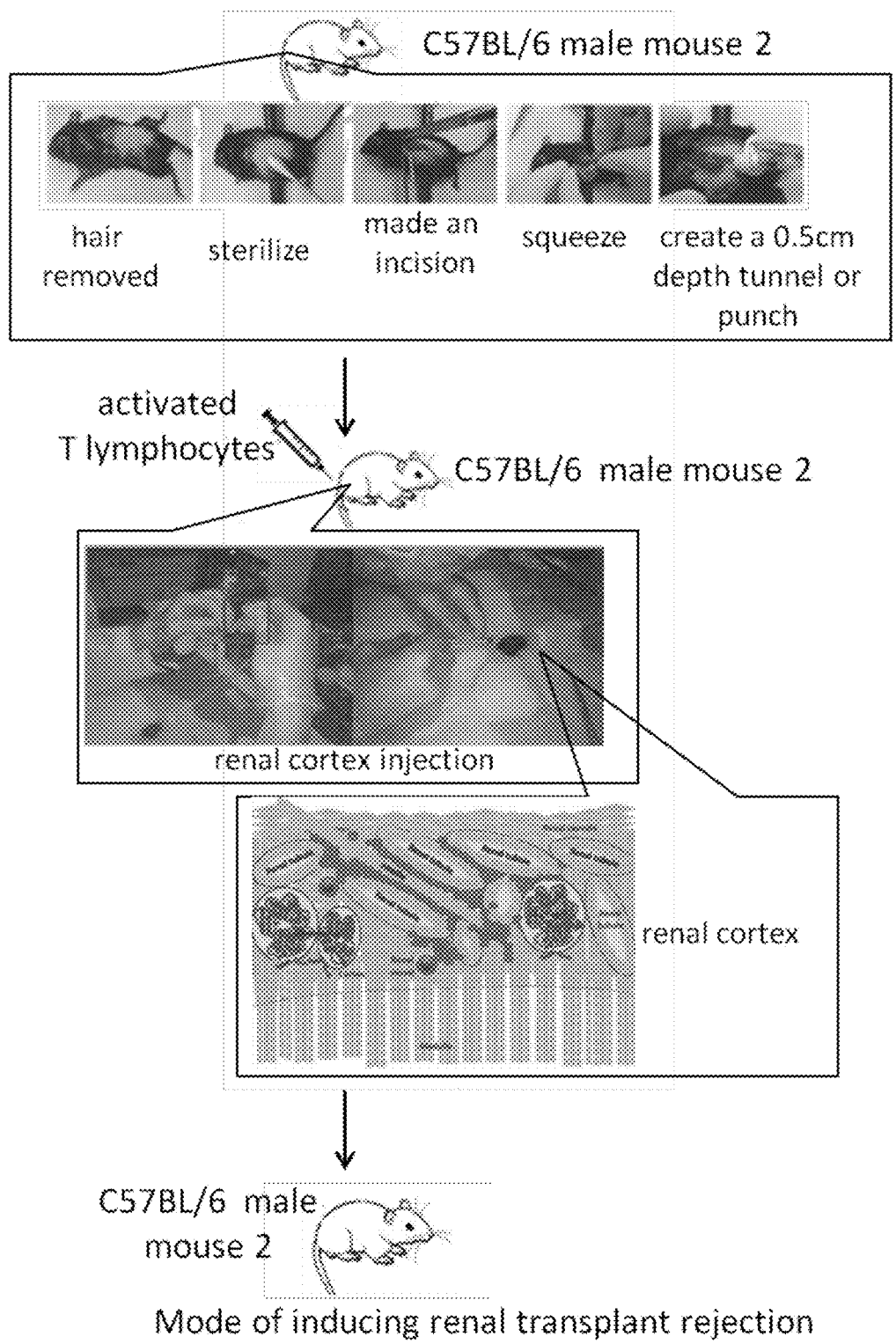
FIG. 3 shows the flow chart of transplantation of in vitro cultured activated T lymphocytes into the renal cortex.
Figure 4:
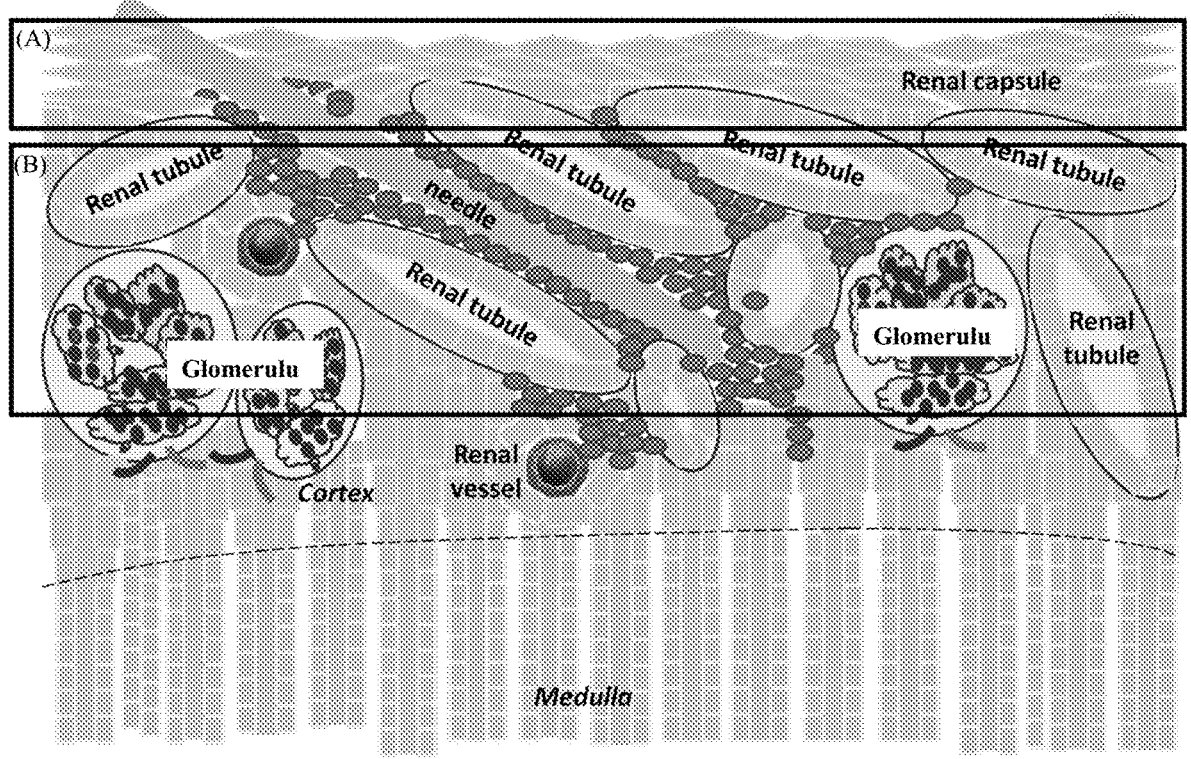
FIG. 4 shows the administration of in vitro activated T lymphocytes in the renal cortex of male mouse (at the needle insertion, the section marked with (B) box), which T lymphocytes attack the renal tissue of the male mouse. In addition, FIG. 4 also indicates that the prior art is usually administered under the renal capsules (the section marked with (A) box).

In order to facilitate the subsequent administration of activated T lymphocytes, we created a tunnel or pouch of the renal cortex in another C57BL/6 male mouse. The surgical process for the manufacture of tunnels or pouches in renal cortex was shown in FIG. 3. The bilateral costal and hypochondriac region of the 6-10 weeks old mice were used for surgery. First, the hair was removed and sterilized. Then we created an opening near the kidney and squeezed out the kidneys with a sterile glove. Next, a needle No. 31 was used to make a 0.2 cm incision, and we injected the mouse kidney cortex along the long diameter to make a 0.5 cm depth tunnel or pouch to facilitate subsequent administration of activated T cells in vivo. $1 \times 10^6$ to $3 \times 10^6$ activated mouse T lymphocytes were counted in a cell counter, and these cells were injected into the tunnel or pouch made in above-mentioned renal cortex of another male mouse. The opening was closed by a superglue to prevent cell loss from the opening, and then we re-confirmed whether it would be lost from the opening. Finally, we sutured the epidermis and muscle layer of the opening (as shown in FIG. 4).

Example 3: Quantification Results from Tissue Slices

Figure 5:
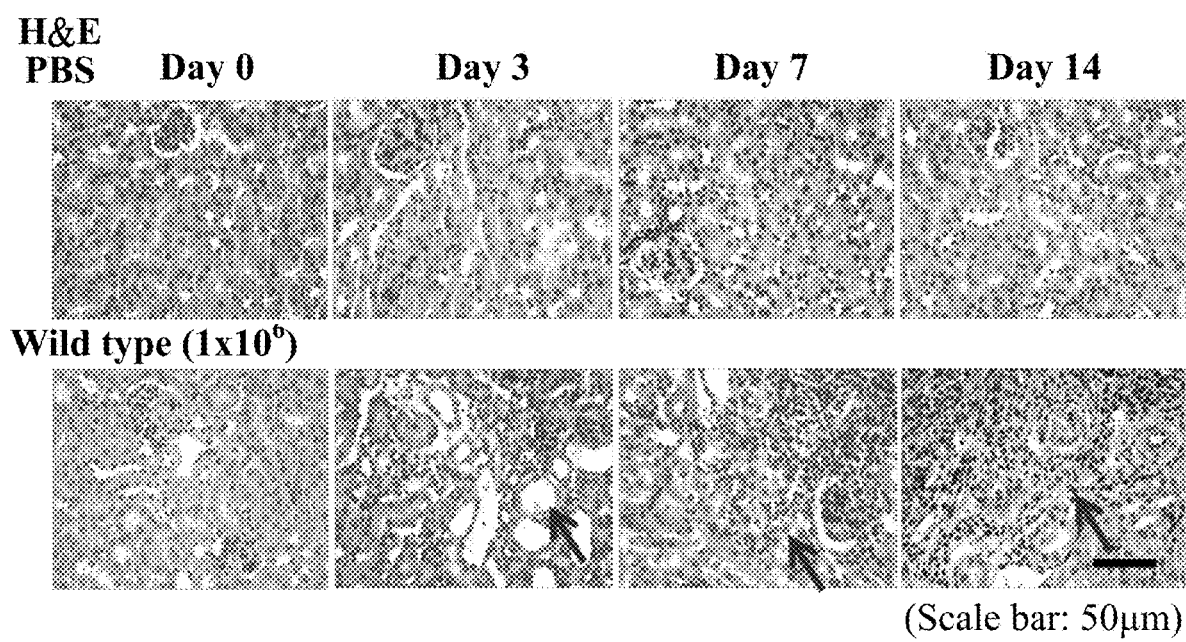
FIG. 5 shows the results of hematoxylin and eosin stain on tissue slices

FIG. 5 showed the results of the hematoxylin and eosin (H & E) stain after the mouse kidney was sliced. The phosphate buffer solution (PBS) was injected into the tunnel or pouch of the renal cortex in the control group. $1 \times 10^6$ activated T cells were injected into the tunnel or pouch of the renal cortex in the experimental group. From 0 to 14th day after injection, the kidney slices from the sacrificed mouse in the control group and in the experimental group were stained. The slices were observed under a 400-fold optical microscope with a scale of 50 μm. The arrows indicated that the renal tubules were not only structurally damaged by severe mononuclear infiltration, but also was found having renal tubular dilatation, renal tubular destruction, and extensive interstitial inflammatory cell infiltration. The results showed continuously pathological change in renal tissue both in control group and experimental group on day 0-day 14. There was no difference in the severity of renal tissue destruction between the experimental group and the control group on day 0 (after PBS or in vitro activated T cells). On day 3 after administration, compared with the control group, the renal tubular structure was significantly dilated, and the renal tubular structure was slightly damaged and renal interstitial inflammatory cell infiltration increased in the experimental group; on day 7 after administration, compared with the control group, the renal tubule was mildly dilated, but extensive destruction of renal tubular structure and renal interstitial inflammatory cells infiltration were found to be significant in experimental group; on day 14 days after administration, compared with the control group, renal tubular dilatation of the experimental group has been reduced, and renal tubular destruction and renal interstitial inflammatory cell infiltration has been slowed down in the experimental group.

Example 4: Mononuclear Cell Infiltration of Renal Tubules

Figure 6:
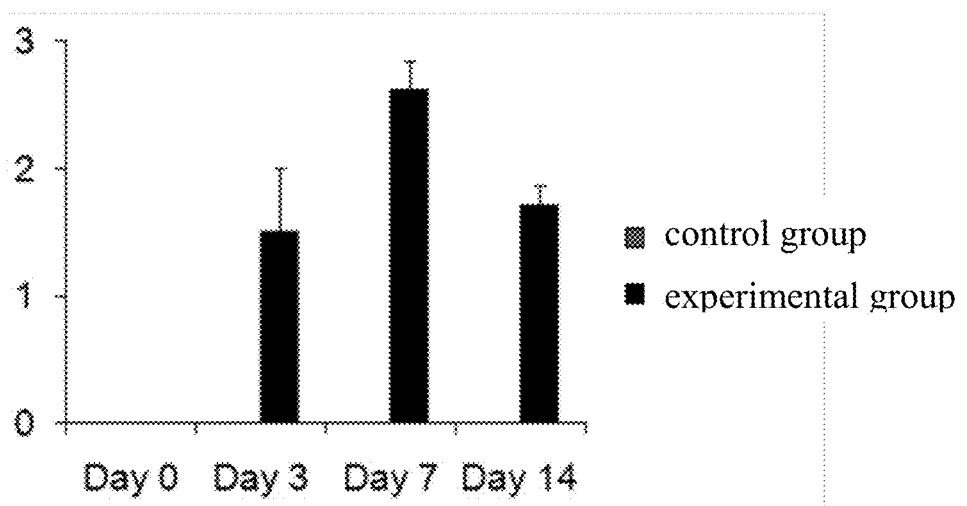
FIG. 6 shows the severity of tubulitis.

FIG. 6 and Table 1 showed the severity of mononuclear cell infiltration of renal tubules which is a sign of inflammatory cell infiltration for transplant rejection. Banff classification: Banff tubulitis classification was according to the degree of severity of kidney rejection. The tubulitis classification criteria were as follows: score 0 represented there was no mononuclear cells in tubular infiltration; score 1 represented 1-4 inflammatory cell infiltration in a renal tubular cross-section containing at least 10 renal tubular epithelial cells; score 2 represented 5-10 inflammatory cell infiltration in a single tubular cross-section; score 3 represented there were more than 10 inflammatory cells in a single tubular cross-section, or at least two of the renal tubular basement membranes were damaged, or 2-3 points in severity of interstitial inflammation, or the severity of the renal tubular inflammation was more than 2 points in other location of kidney sections. The control group was the mouse injected with phosphate buffer solution (PBS) in the renal cortical tunnels or pouches; the experimental group was the mouse injected with $1 \times 10^6$ activated T cells in the renal cortical tunnels or pouches, and then those animals were sacrificed in due date (day 0, 3, 7, 14), the kidney tissue slices were stained with hematoxylin and eosin (H&E) for observation of the mononuclear cell infiltration and classified as 0-3 level according to the Banff classification guideline.

The results showed that the score in the control group were 0 which represented that there was no renal tubular inflammation in different days without the appearance of activated T cells. While the score in the experimental group on the first 3 days was 1.5±0.5, which represented that the destruction of the host kidney tissue has a certain extent on the third day after transplantation of activated T cell; the score of the mice in the experimental group on day 7 was 2.6±0.2, which represented the transplantation of activated T cells had the highest destructive function on the host kidney on day 7; the score in the experimental group on day 14 was 1.7±0.2 which indicated that the destruction of the organ has been lightened. The reason of declining in scores on day 14 was due to the self-repair capacity by mouse immune cells.

TABLE 1

Banff tubulitis classification

|  | Mean | SEM |
|---|---|---|
| Control group (PBS) | | |
| Day 0 | .0 | .0 |
| Day 3 | .0 | .0 |
| Day 7 | .0 | .0 |
| Day 14 | .0 | .0 |
| Experimental group (Wild type) | | |
| Day 0 | 0 | 0 |
| Day 3 | 1.5 | 0.5 |
| Day 7 | 2.6 | 0.2 |
| Day 14 | 1.7 | 0.2 |

SEM: standard error of the mean

Example 5: Mononuclear Cell Infiltration in Renal Interstitium

Figure 7:
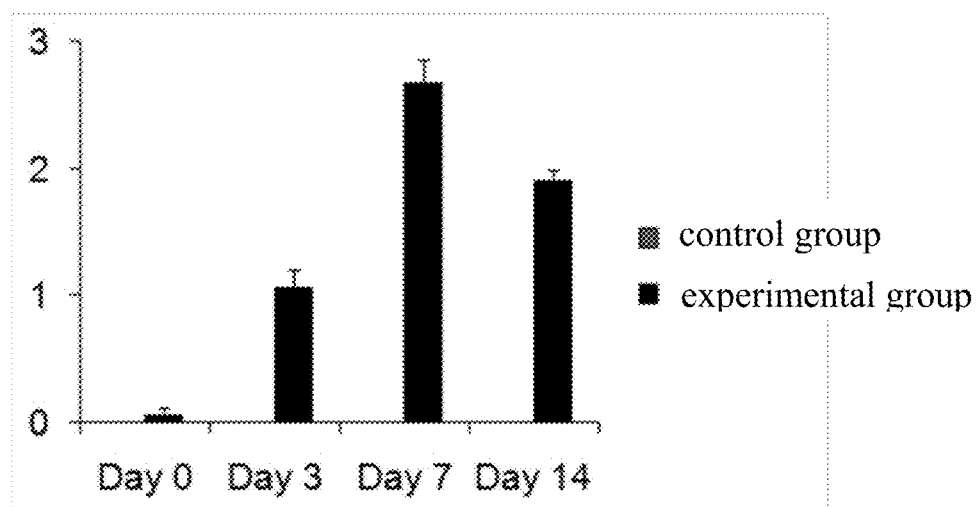
FIG. 7 shows the severity of renal interstitial mononuclear leukocyte infiltration.

FIG. 7 and Table 2 showed the severity of mononuclear cell infiltration in renal interstitium, which is also a sign of inflammatory cell infiltration for transplant rejection. Banff classification: Banff classification for interstitial inflammation was according to the degree of severity of transplant rejection. The classification criteria were as follows: score 0 represented no or trivial mononuclear cells in tubular interstitium within <10% unscarred area; score 1 represented mononuclear cell infiltration in 10-25% renal interstitium; score 2 represented mononuclear cell infiltration in 25-50% renal interstitium; score 3 represented mononuclear cell infiltration in >50% renal interstitium. The control group was the mouse injected with phosphate buffer solution (PBS) in the renal cortical tunnels or pouches; the experimental group was the mouse injected with $1 \times 10^6$ activated T cells in the renal cortical tunnels or pouches, and then those mice were sacrificed in due date (day 0, 3, 7, 14), the kidney tissue slices were stained with hematoxylin and eosin (H&E) for observation of the mononuclear cell infiltration and classified as 0-3 level according to the Banff classification guideline.

The results showed that the score in the control group were 0 which represented that there was no inflammatory cell in renal interstitium in different days without the appearance of activated T cells. While the score in the experimental group on the first 3 days was 1.1±0.1 which represented that the destruction of the host kidney tissue was 10-25% on day 3 after transplantation of activated T cell; the score of the mice in the experimental group on day 7 was 2.7±0.2 which represented the transplantation of activatited T cells had reached the highest destruction on the host kidney on day 7; the score in the experimental group on day 14 were 1.9±0.1 which represented the destruction of activated T cells on the organ has been lightened. The reason of declining in scores on day 14 was due to the self-repair capacity by mouse immune cells.

TABLE 2

Banff classification for interstitial mononuclear leukocyte infiltration

|  | Mean | SEM |
|---|---|---|
| Control group (PBS) | | |
| Day 0 | .0 | .0 |
| Day 3 | .0 | .0 |
| Day 7 | .0 | .0 |
| Day 14 | .0 | .0 |
| Experimental group (Wild type) | | |
| Day 0 | 0.1 | 0.1 |
| Day 3 | 1.1 | 0.1 |
| Day 7 | 2.7 | 0.2 |
| Day 14 | 1.9 | 0.1 |

There are problems of time consuming with high animal mortality and insufficient reproducibility during the manufacturing the animal model simulating the transplant rejection reaction. To resolve above mentioned problems, the present invention provides a novel animal model simulating the transplant rejection successfully.

What is claimed is:

1. A method for preparing an animal model simulating a transplant rejection, which includes:
    (a) providing a dendritic cell, wherein the dendritic cell is obtained from a first animal subject;
    (b) providing a lymphocyte, wherein the lymphocyte is selected from a second animal subject;
    (c) co-culturing the dendritic cell and lymphocyte in vitro to form an activated T lymphocyte;
    (d) creating an implant position in renal cortex of a third animal subject; and
    (e) transplanting the activated T lymphocyte into the implant position in the renal cortex of the third animal subject;
    wherein the first subject, the second subject, and the third subject are same species, and the activated T lymphocyte would attack the renal cortex after being transplanted into the implant position in the renal cortex of the third animal subject, thus a transplant rejection model in animals would be induced in the third animal subject.

2. The method of claim 1, wherein the first animal subject, the second animal subject, and the third animal subject are mice.

3. The method of claim 1, wherein the gender of the first animal subject and the second animal subject are different.

4. The method of claim 3, wherein the first animal subject is a male mouse and the second animal subject is a female mouse.

5. The method of claim 1, wherein the implant position is a tunnel or a pouch.

6. The method of claim 1, wherein the lymphocyte is a $CD4^+$ entity or a $CD8^+$ entity.

7. The method of claim 1, wherein the dendritic cell is obtained from a thigh bone marrow of the first animal subject.

8. The method of claim 1, wherein the dendritic cell is obtained from a lymph node of the first animal subject.

9. The method of claim 5, wherein a depth of the tunnel or a pouch is 0.5 cm.

10. The method of claim 2, wherein an age of the mouse is 6-10 weeks old.

\* \* \* \* \*